United States Patent
Ponomarenko et al.

(10) Patent No.: US 8,030,536 B2
(45) Date of Patent: Oct. 4, 2011

(54) ABSORBENT ARTICLES WITH SUBLAYER

(75) Inventors: Ekatarina Anatolyevna Ponomarenko, Bad Soden (DE); Monika Imgard Johanning, Steinbach/Ts (DE); Ralf Geilich, Eppstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 279 days.

(21) Appl. No.: 11/525,613

(22) Filed: Sep. 22, 2006

(65) Prior Publication Data

US 2010/0228215 A1 Sep. 9, 2010

(30) Foreign Application Priority Data

Sep. 23, 2005 (EP) ..................................... 05108798

(51) Int. Cl.
*A61F 13/15* (2006.01)
(52) U.S. Cl. .................. 604/383; 604/378; 604/385.101
(58) Field of Classification Search .................. 604/378, 604/383, 348, 354, 385.101
See application file for complete search history.

(56) References Cited

U.S. PATENT DOCUMENTS

| 3,860,003 A | 1/1975 | Buell |
| 4,610,678 A | 9/1986 | Weisman et al. |
| 4,834,735 A | 5/1989 | Alemany et al. |
| 4,940,464 A | 7/1990 | Van Gompel et al. |
| 5,092,861 A | 3/1992 | Nomura et al. |
| 5,151,092 A | 9/1992 | Buell et al. |
| 5,246,433 A | 9/1993 | Hasse et al. |
| 5,260,345 A | 11/1993 | DesMarais et al. |
| 5,342,338 A | 8/1994 | Roe |
| 5,387,207 A | 2/1995 | Dyer et al. |
| 5,397,316 A | 3/1995 | LaVon et al. |
| 5,509,914 A * | 4/1996 | Osborn, III .................. 604/368 |
| 5,533,991 A | 7/1996 | Kirby et al. |
| 5,554,145 A | 9/1996 | Roe et al. |
| 5,569,234 A | 10/1996 | Buell et al. |
| 5,603,707 A * | 2/1997 | Trombetta et al. ............ 604/383 |
| 5,625,222 A | 4/1997 | Yoneda et al. |
| 5,628,097 A | 5/1997 | Benson et al. |
| 5,658,639 A | 8/1997 | Curro et al. |
| 5,885,267 A * | 3/1999 | Mishima et al. .............. 604/378 |
| 5,897,545 A | 4/1999 | Kline et al. |
| 5,916,661 A | 6/1999 | Benson et al. |

(Continued)

FOREIGN PATENT DOCUMENTS

EP 0 203 823 A2 12/1986

(Continued)

OTHER PUBLICATIONS

International Search Report.

*Primary Examiner* — Lynne Anderson
(74) *Attorney, Agent, or Firm* — John G. Powell

(57) ABSTRACT

A diaper or adult incontinence garment including a backsheet and a sublayer. The sublayer may include one or more acquisition layers and one or more regions having a multitude of through or blind holes. The sublayer may isolate feces away from the skin and at the same time provide liquid acquisition. Certain regions of the sublayer may have a total open area of from 10% to 50% of the total surface area of the sublayer. The holes have an average smallest dimension of at least 3 mm. The sublayer has an average caliper of from 2 mm to 6, and an average caliper loss after wetting and under pressure of 0.3 psi of less than 20%.

6 Claims, 4 Drawing Sheets

U.S. PATENT DOCUMENTS

| | | |
|---|---|---|
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,414,215 B1 * | 7/2002 | Roe ................. 604/378 |
| 6,423,884 B1 | 7/2002 | Oehmen |
| 6,443,940 B1 * | 9/2002 | Ashton et al. ........... 604/396 |
| 6,458,111 B1 | 10/2002 | Onishi et al. |
| 6,528,698 B2 | 3/2003 | Mizutani et al. |
| 6,786,894 B2 * | 9/2004 | Divo et al. ............ 604/385.101 |
| 6,897,350 B2 | 5/2005 | Yagou et al. |
| 7,005,558 B1 * | 2/2006 | Johansson et al. ........... 604/383 |
| 7,067,711 B2 | 6/2006 | Kuroda et al. |
| 7,179,952 B2 * | 2/2007 | Vukos et al. ................. 604/378 |
| 2003/0045851 A1 * | 3/2003 | Vartiainen ............... 604/378 |
| 2003/0093048 A1 | 5/2003 | McBride |
| 2003/0139719 A1 | 7/2003 | Nanaumi et al. |
| 2003/0187417 A1 | 10/2003 | Kudo et al. |
| 2003/0233082 A1 | 12/2003 | Kline et al. |
| 2004/0167486 A1 | 8/2004 | Busam et al. |
| 2005/0234410 A1 | 10/2005 | Ashton et al. |
| 2005/0256475 A1 | 11/2005 | Komatsu et al. |

FOREIGN PATENT DOCUMENTS

| | | |
|---|---|---|
| EP | 0 953 324 A1 | 11/1999 |
| EP | 1 201 212 A2 | 5/2002 |
| WO | WO 90/14813 A1 | 12/1990 |

* cited by examiner

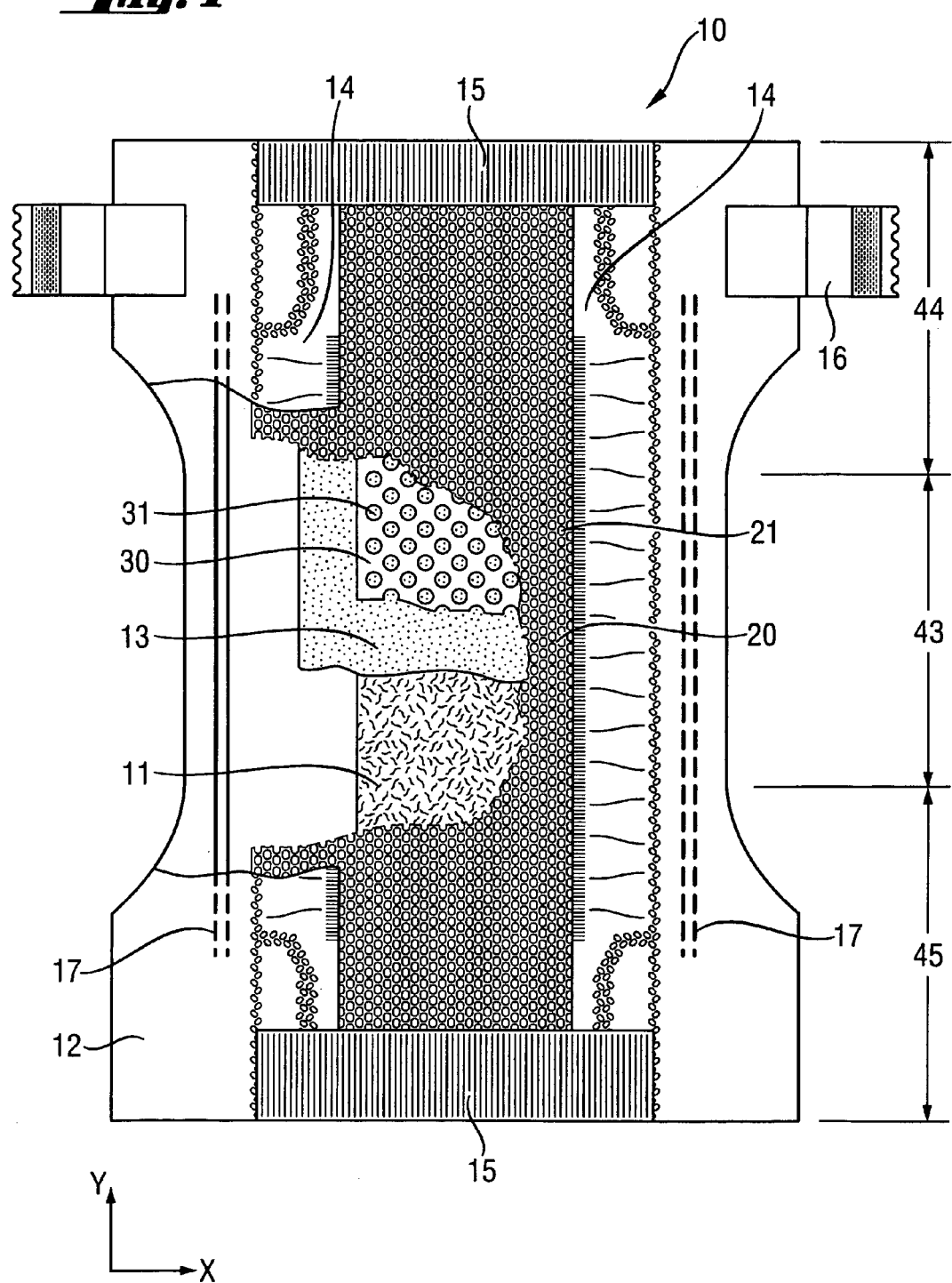

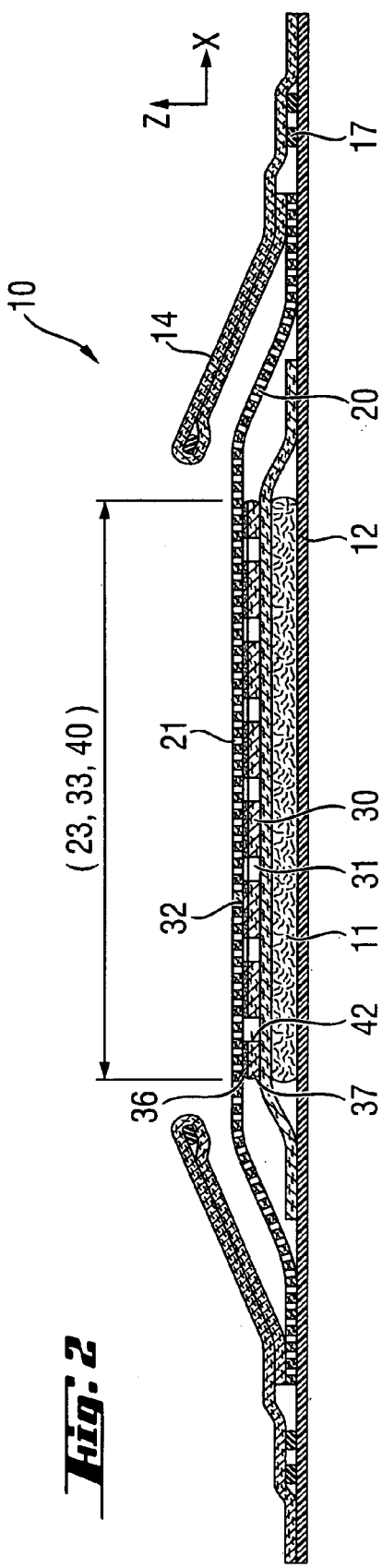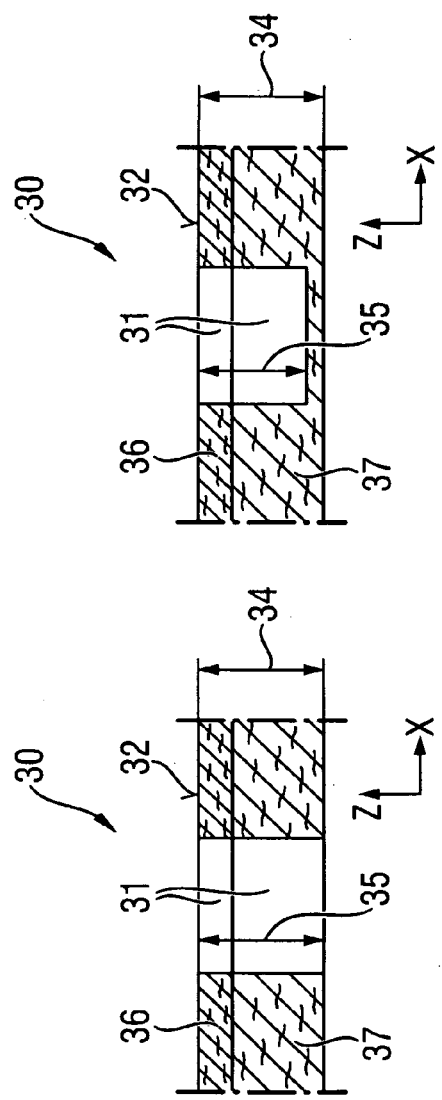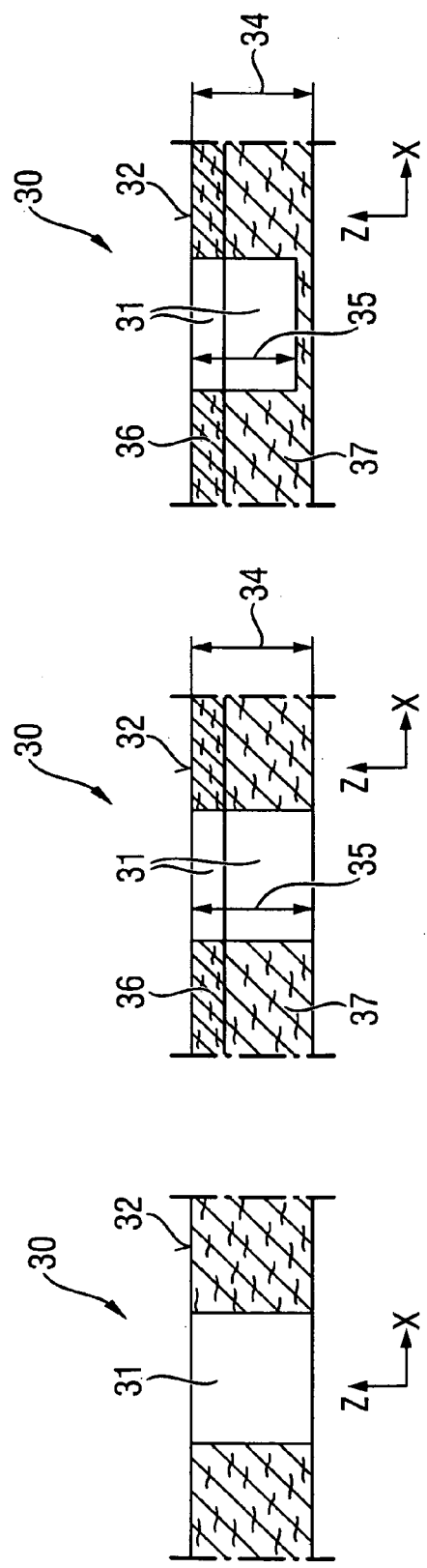

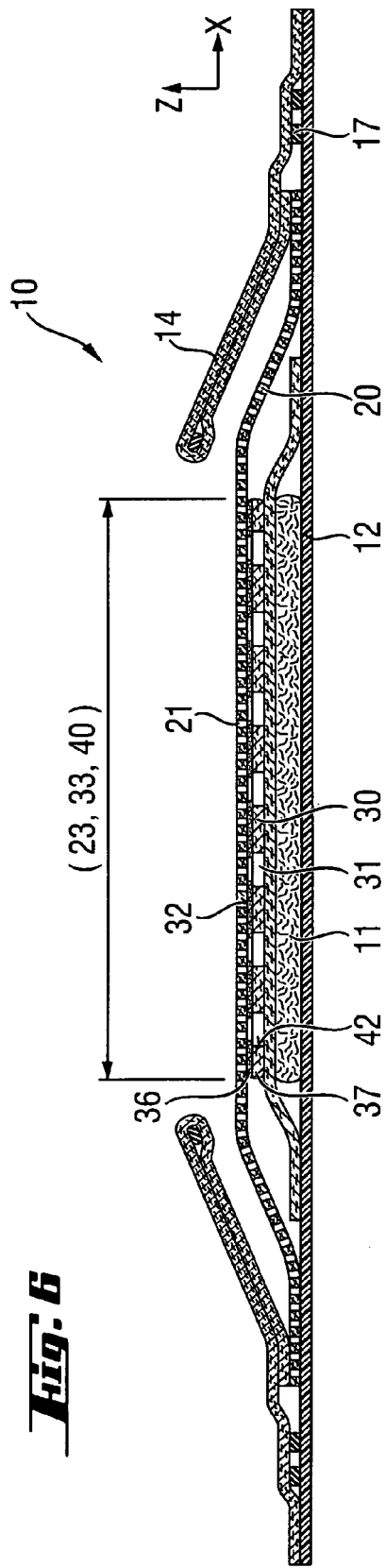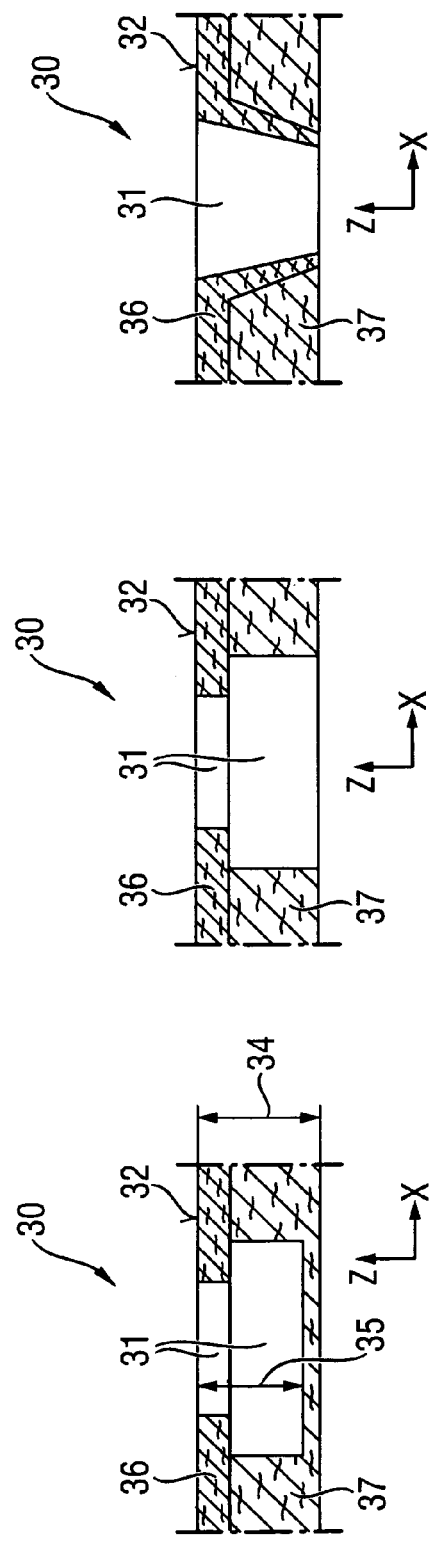

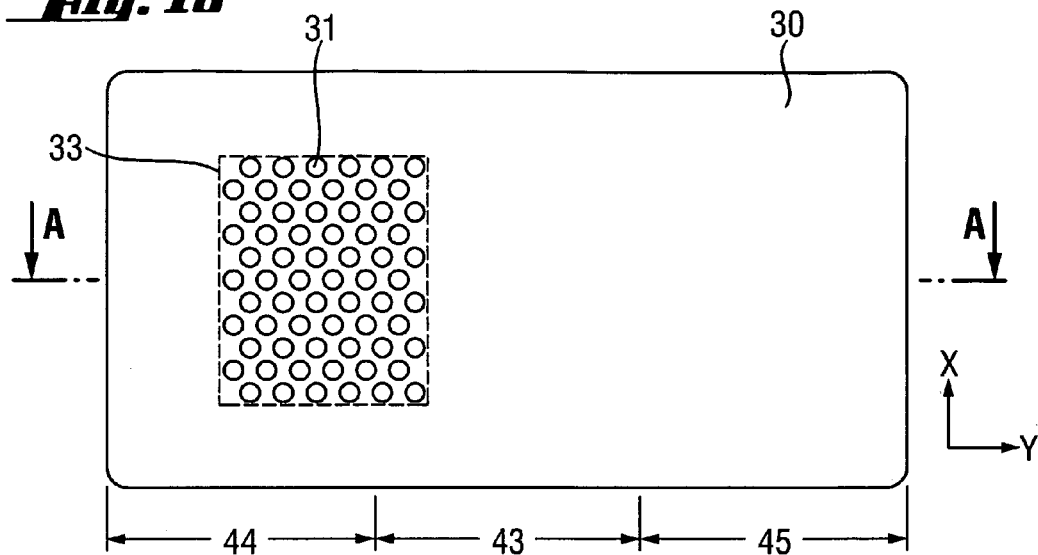
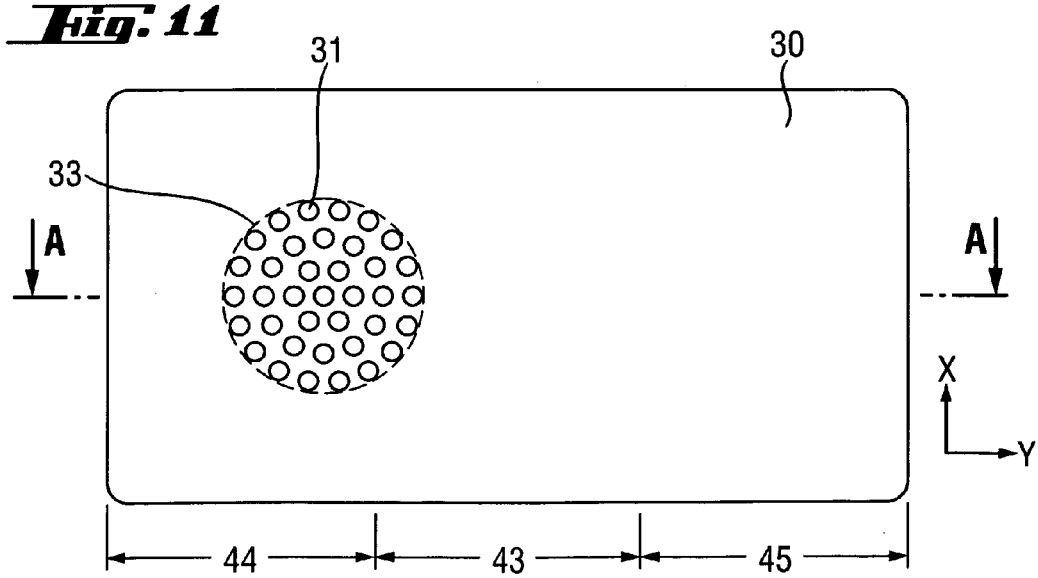
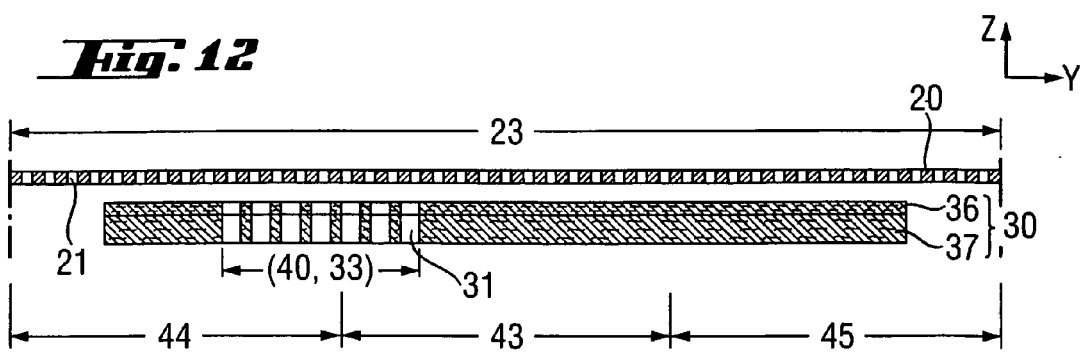

ABSORBENT ARTICLES WITH SUBLAYER

FIELD OF THE INVENTION

This invention is directed to a diaper (including training pants) or adult incontinence garment, having a backsheet, an absorbent core and topsheet and a sublayer (30), said sublayer comprising holes with an average smallest dimension (as defined herein) of at least 3 mm, and said sublayer having an average caliper of from 2 mm to 6, and said sublayer having an average caliper loss (wet resilience) after wetting and under pressure of 0.3 psi, as defined herein, of less than 20%, said sublayer providing a very efficient isolation of feces away from the skin and at the same time liquid acquisition.

BACKGROUND OF THE INVENTION

It is well known that fecal material is often difficult to remove from the skin of the user, in particular on sensitive skin such as by young babies and the skin around the genitals. Moreover, it is well known that fecal material on the skin can cause irritation and redness of the skin and some times even dermatitis of the skin.

One of the solutions to reduce the fecal material on the skin is to provide a means to isolate the fecal material immediately after discharge, away from the skin. The problem with feces isolation in diapers is that the feces can vary hugely in consistency and viscosity and furthermore that, whilst isolating the feces, the diaper needs to retain its urine absorption capacity.

Hereto, diapers have been suggested with a topsheet with one or more large openings, through which the feces can pass to a void space between the topsheet and the absorbent core. The fecal material is then stored underneath this topsheet, away from the skin.

As alternative, a diaper with a first topsheet with a multitude of small openings has been proposed, allowing low viscosity feces to pass through said openings onto the absorbent core, such that it may be isolated underneath said topsheet and such that the absorbent core may dewater the feces, such as for example described in U.S. Pat. No. 5,342,338. Optionally, a second topsheet with openings may be present, which further allows immobilization of the feces and dewatering of the feces by the absorbent core underneath.

Also various other feces management element that comprise high loft or loop materials have been proposed.

The inventors have now found a very efficient, improved way to provide i) feces isolation and immobilization, ii) reduced re-soiling of the skin by the immobilized feces and ii) good liquid acquisition at the same time. This is achieved by providing an absorbent article, e.g. diaper, comprises a sublayer that comprises at least one, but preferably at least two acquisition layers with holes therein, said holes being capable to receive and store and immobilize feces, and said sublayer being at the same time capable to acquire the liquid (urine). Furthermore, the inventors found that it is important that the sublayer has a certain open areas in order to provide efficient and effective feces immobilization and liquid acquisition at the same time, and that the holes of the sublayer should have a large enough size and caliper to provide enough storage volume for the feces.

Moreover, they found that it is highly important for the sublayers of the present invention, which have a liquid acquisition and possibly even a liquid distribution function, that such sublayers maintain their volume (e.g. caliper) in use, i.e. that the sublayer is pressure resistant and resilient even when wet and even when the user may put pressure on it. The importance of pressure resistant feces management elements and elements with a certain caliper have been described in the art, but there has not been any teaching or realization that such feces management elements should be such that they maintain the same volume after they have acquired liquid (urine).

Thus, a diaper with a sublayer is obtained that provide a better feces immobilization whilst still allowing excellent liquid acquisition and comfortable fit.

SUMMARY OF THE INVENTION

The invention relates to a diaper or adult incontinence garment (10) comprising a backsheet (12) and a sublayer (30) for acquisition of bodily exudates and storage of feces, comprising at least a first acquisition layer (37) and optionally a second (36) and further acquisition layers, and said member comprising one or more regions (43) with a multitude of through or blind holes (31), said region(s) having a total open area of from 10% to 50% of the total surface area of said sublayer (30) (as measured on the surface facing the user), said sublayer (30) and holes (31) having a length in y-direction, width in x-direction and thickness (caliper) in z-direction, said holes (31) having an average smallest dimension, in the x-y cross section of the holes (31) in the surface of said sublayer (30), facing the user in use, of at least 3 mm, and said sublayer (30) having an average caliper (34) of from 2 mm to 6, and whereby said sublayer (30) has an average caliper loss (wet resilience) after wetting and under pressure of 0.3 psi, as defined herein, of less than 20%, preferably 12% or less , or even more preferably 8% or less.

The first acquisition layer (37) of the sublayer (30) comprises preferably partially bonded or non-boned polyester fibers and/or stiffened curled cellulose fibers, optionally mixed with pulp.

Preferably, the sublayer comprises more than one acquisition layer, and preferred may be that it comprises a second acquisition layer (36) at least on top of the first acquisition layer (37) (i.e. between the user and the first acquisition layer). Said second acquisition layer may preferably be bonded nonwoven layer, preferably a carded bonded nonwoven layer. This not only may improve the feces immobilization and liquid acquisition, but it may also help to avoid contact of the fibers of the first acquisition layer with the skin.

The sublayer (30) may be obtained by forming holes (31) into a sublayer (30) material by any known hole-forming method, but a preferred method includes the steps of:
a) providing a first acquisition layer (37) with holes in it or through it;
b) placing a second acquisition layer (36) onto the first acquisition layer (37); and either
c) pushing parts of the second layer (36) into the holes of the first layer (37) and/or pulling parts of the second layer (36) into the holes of the first layer (37) e.g. by vacuum), thereby forming indentations in said second layer (36), and thereby forming the combined holes (31); or
c) punching or pushing holes in the second layer (36) such that parts of the second layer (36) are folded onto the z-direction side walls of the holes in the first acquisition layer (37).

BRIEF DESCRIPTION OF THE DRAWINGS

FIG. 1 is a plan top view of a diaper (10) of the invention, with cut out portions to show the sublayer (30) as described herein.

FIG. 2 shows a cross-section view of the diaper (10) of FIG. 1 through the x-direction centre line thereof.

FIG. 3 shows a cross section through a hole (31) and surrounding parts of a sublayer (30) of the diaper (10) of the invention.

FIG. 4 shows a cross section through a hole (31) and surrounding parts of another preferred sublayer (30) herein.

FIG. 5 shows a cross section through a hole (31) and surrounding parts of another sublayer (30) herein.

FIG. 6 shows a cross-section view of the diaper (10) with another preferred sublayer (30), taken through the x-direction centre line thereof.

FIG. 7 shows a cross section through a hole (31) and surrounding parts of yet another preferred sublayer (31) herein.

FIG. 8 shows a cross section through a hole (31) and surrounding parts of yet another preferred sublayer (30) herein, as also shown in FIG. 6.

FIG. 9 shows a cross section through a hole (31) and surrounding parts of yet another preferred sublayer (31) herein FIG. 10 shows a plan top view of preferred sublayer (30) for use herein having a rectangular region (33) with holes with a circular circumference in the back region (44) and partial crotch region (43) of the diaper (10).

FIG. 11 shows a plan top view of preferred sublayer (30) for use herein having a circular region (33) with holes with a circular circumference in the back region (44) and partial crotch region (43) of the diaper (10).

FIG. 12 shows a cross section view of the sublayer (30) of FIG. 11 and a topsheet (20), taken along the y-direction centre line thereof, forming an overlap region (40).

DETAILED DESCRIPTION OF THE INVENTION

Whilst the invention has been derived while investigating improved feces isolation and immobilization, the sublayer (30) as described herein may also be used in articles other than those intended for feces handling, for example in sanitary napkins or even panty-liners When used herein, "diaper" means any article intended for use by a baby or infant for collection of feces and/or urine, including, amongst others, also training pants. "Adult incontinence garment", when used herein, includes any article intended for adults for collection of feces and/or urine. In description the word "diaper" will be used, but this will include adult incontinence garments, unless otherwise indicated.

When used herein the minimum dimension and the surface area of the holes (31) and the open area of the regions (33) are determined on the surface of the sublayer (30) facing the user or the topsheet (20), when present, unless otherwise stated.

The surface area of the overlap-zone (40) and the open area of the overlap-zones (40), described below, are determined on the surface of the topsheet (20), facing the user in use.

The diaper (10) and components thereof, e.g. the backsheet (11), topsheet (20) and sublayer (30) herein, have a length in longitudinal or y-direction (or Machine Direction), a width in transverse or x-direction (or Cross Machine Direction) and a thickness or caliper in z-direction, as shown in the Figures.

The diaper (10) and optionally components thereof has a back region (44), crotch region (43) and front region (45), that in use are positioned towards the back, in the crotch, or towards the front of the user, respectively. They typically represent herein each ⅓ of the length of the diaper.

The surface area of the aperture (21) and combined hole (31), as referred to herein, and as used herein to obtain the open area values herein, is the surface area of the cross-section of the aperture (21) or combined hole (31) in the plane of the body-facing surface of the topsheet (20) and the body-facing surface (32) of the sublayer (30), respectively. The average minimum and maximum dimensions of the apertures and holes (31) as used herein is also determined in the cross-section of the aperture (21) or hole (31) in the plane of the body-facing surface of the topsheet (20) and of the sublayer (30).

FIG. 1 is a plan view of a preferred diaper (10) according to the present invention. The diaper is shown in its flat out, uncontracted state (i.e., without elastic induced contraction). Portions of the structure are cut away to more clearly show the underlying structure of the diaper (10). The portion of the diaper (10) that contacts a wearer is facing the viewer.

The diaper (10) comprises a topsheet (20), as described hereinafter in detail, a backsheet (12), and typically an absorbent core (11), and optionally a core wrapping material (13), and a sublayer (30), as described herein after in detail. Further optional features may be present, such elasticized leg cuffs or elastics (17), barrier cuffs (14), elastic waist feature(s) (15). One end portion of the diaper (10) is configured as a first or front (waist) region (45) of the diaper (10). The opposite end portion is configured as a second, back (waist) region (44) of the diaper (10). An intermediate portion of the diaper (10) is configured as a crotch region (43), which extends longitudinally between the first and second waist regions (44, 45). The crotch region (43) is that portion of the diaper (10) which, when the diaper (10) is worn, is generally positioned between the wearer's legs. The diaper (10) is depicted with its longitudinal axis (Y) and its transverse axis (X). The diaper may also comprise a fastening system, which may include at least one fastening member (16) and at least one landing zone (not shown). Preferred diaper configurations are described generally in U.S. Pat. Nos. 4,940,464; 5,554,145; 5,569,234; 6,004, 306, U.S. patent application Ser. No. 10/171,249 and in U.S. patent application Ser. No. 10/824,121.

The absorbent core (11) in FIG. 1 is disposed between the sublayer (30) and the backsheet (12). The absorbent core (11) may comprise any absorbent material that is generally compressible, conformable, non-irritating to the wearer's skin, and capable of absorbing and retaining liquids such as urine. Exemplary absorbent core structures (11) for use as the absorbent articles (10) herein are for example described in U.S. Pat. Nos. 4,610,678; 4,834,735; 5,260,345; 5,387,207; 5,397,316; and 5,625,222. Preferably, the absorbent core (11) comprises at least a super absorbent material, preferably a superabsorbent polymer material, also referred to as SAP or AGM, that is capable of absorbing at least about 5 times, preferably at least 10 times, its weight of an aqueous fluid such as 0.9% saline as measured using the Centrifuge Retention Capacity test, well known in the art.

The absorbent material in the absorbent core (11) may have a "profiled" distribution, whereby the absorbent core comprises more absorbent material in one area (e.g. the p-point or crotch and optionally front region) than in another area (e.g. back region).

The absorbent core (11) may also comprise a structuring agent or matrix agent, such as absorbent fibrous material, such as airfelt fibers, and/or adhesive, which each may serve to immobilize the water-swellable material.

However, it may be preferred that a relatively low amount or no absorbent fibrous (cellulose) material is used in the absorbent core (11). Thus, it may be preferred that said core (11) herein comprises large amounts of the water-swellable material and only very little or no absorbent (cellulose) fibers, preferably less than 20% by weight of the water-swellable material, or even less than 10% by weight of the water-swellable material, or even less than 5% by weight.

Preferred absorbent cores (11) herein comprise an adhesive or thermoplastic material or preferably a (fibrous) thermoplastic adhesive material, which is laid down onto a layer of water- absorbing and/ or-swellable material. Thereby, the thermoplastic or adhesive material provides cavities to hold the water-swellable material and thereby immobilizes this material. Also, the thermoplastic or adhesive material bonds to the substrate and thus affixes the water-swellable material to the substrate. It may be preferred that no absorbent fibrous material is present in the absorbent core (11).

A particularly preferred absorbent core (11) for liquid (e.g. urine) storage is described in U.S. patent application Ser. No. 10/776,839.

The backsheet (12) is preferably joined to the topsheet (20), and optionally the sublayer (30) at least about a portion of the periphery thereof. The backsheet (12) is preferably manufactured from at least a (thin) polymer film. In one preferred embodiment the film comprising backsheet (12) is impervious to liquids. Typically, the backsheet (12) comprises a layer of polyethylene film having a basis weight between about 10 g/m² and about 30 g/m², although other flexible, liquid impervious materials can be used. Preferably, the film is breathable (e.g. via micropores) so as to permit vapors to escape from the diaper (10) while still preventing exudates from passing through the backsheet (12). Particularly preferred backsheet materials have a nonwoven laminated to the film layer so as to make backsheet (12) more "cloth-like". Such a nonwoven layer may comprise a nonwoven material (e.g. one having a spunbonded or other suitable structure) with a basis weight between about 15 g/m² and about 25 g/m². Suitable materials for use as backsheet (12) are available form Clopay Plastic Products Company of Mason, Ohio.

The diaper (10) may also include such other features (not shown) as are known in the art including front and rear ear panels, waist cap features, elastics, topsheet (20)s with aperture(s) and elastics, and the like to provide better fit, containment and aesthetic characteristics. Such additional features are well known in the art and are e.g., described in U.S. Pat. Nos. 3,860,003 and 5,151,092 and EP1201212-A.

The preferred absorbent diapers herein are refastenable diapers (10) (diapers with fasteners) and pant-type diapers, i.e. training pants. Suitable pant-type diapers are disclosed in U.S. Pat. Nos. 5,246,433; 5,569,234; 6,120,487; 6,120,489; 4,940,464; 5,092,861; 5,897,545; 5,957,908 and in Published US Pat. Application 2003/0233082A1.

Sublayer (30)

The sublayer (30) herein is (serves as) an acquisition layer and optionally also (as) a distribution layer, capable to acquire liquid (urine) and temporarily hold the liquid and allow it to pass, or transport it to the absorbent core underneath (in Z-direction), and optionally also distribute it in the X and Y direction of the sublayer (30). It typically does not serve to hold or store fluid (urine) for a longer period or permanently, but it facilitates the absorption of the fluid by the absorbent core below. However, the sublayer of the diaper (10) of the invention does serve to store and/or immobilize fecal material in the holes (31) of the sublayer (30).

The sublayer (30) herein is thereto typically hydrophilic and it typically does not comprise any super-absorbent materials, or water-swelling materials, such as generally referred to as SAP and AGM particles, further described herein above.

The sublayer (30) comprises typically a fibrous layer, and it comprises preferably two layers or more that are fibrous layers. This is further shown in FIGS. 2, 4 to 9 and 12.

The holes (31) of the sublayer (30) herein are capable to store and immobilize feces and they include blind holes (31), as for example shown in FIGS. 5 and 7, and through holes (31), as for example shown in FIGS. 1 to 4, 6, 8, 9 and 12. When the holes (31) are blind holes (31), it is still preferred that the holes (31) have an average depth or caliper that is about 50% to 95% of the average thickness or caliper of the relevant region of the sublayer (30) with said holes (31), or the average thickness or caliper of the sublayer (30) as a whole. If the sublayer (30) comprises two or more layers, then the sublayer holes (31) referred to herein are preferably through or in two or more layers The holes (31) of the sublayer (30) have an average smallest dimension of 3 mm, preferably up to 10 mm, preferably from 4 mm to 10 mm, or more preferably from 4 mm to 8 mm, or even more preferably from 5 mm to 7 mm, said average being the average over the total of smallest dimensions of the holes (31) in the sublayer (30). This can be determined by the method described herein below.

The circumference of the holes (31) of the sublayer (30) may have any form, including rectangular (so that the holes (31) are in the form of stripes or channels), but preferably the holes (31) are square, oval, or more preferably the sublayer (30) comprises holes (31) with a circular circumference, including thus preferably substantially cylindrical holes (31), as shown in FIGS. 1, 10 and 11.

Preferably, a hole is such that the smallest dimension is through the centre point of said hole.

The average shortest (smallest) distance between neighboring holes (31) (from edge to edge, in the plane of the surface facing the topsheet) is preferably from 2 mm to 10 mm, or more preferably from 3 mm to 7 mm.

The region of the sublayer (30) with said holes (310) is herein referred to as "region (33)"; said region (33) has preferably an open area of from 10% to 50% of the total surface are area of the sublayer (30) (whereby the open area is the sum of the surface areas of the holes (31) as measured in the cross section of the holes in or on the surface (32) of the sublayer (30) that faces the topsheet (20)). Preferably the open area of a region (33) with holes (31) of the sublayer (30) is from 15% to 45% or even more preferably from 25% to 40% or to 35% of the total surface area the sublayer (30).

The sublayer (30) may comprise one or more regions with holes (31), typically such that the region(s) is (are) at least present in the crotch and/or back region of the sublayer (30), as shown in FIGS. 10 and 11.

In one preferred execution, shown in FIGS. 10 and 11, the sublayer (30) comprises a single region (33) with holes (31), typically in the back region (44) and part of the crotch region (43) of the diaper, e.g. the back ⅔ or 65% or less of the surface area of the topsheet or diaper (10), preferably the back 60% or even more preferably the back 50% thereof. Thus, preferably, the region or regions (33) form at least 30%, more preferably at least 35% of the total surface area of the sublayer (30), and preferably at the most 65%, or even at the most 60% of said surface area of the sublayer.

Preferably, the surfaces of the sublayer (30) that face the topsheet and the absorbent core are flat.

When the holes (31) in the sublayer (30) are blind holes (31), then the holes (31) typically have an average caliper or depth that is at least 70%, or preferably at least 80%, or when possible even at least 95% of the average caliper of the sublayer (30).

The sublayer (30) has preferably an average caliper or depth (34, 35) of at least 2 mm, preferably at least 3 mm, or even at least 4 mm. The preferred maximum caliper of the sublayer may be 6 mm, for wearer's comfort.

The caliper or depth (35) of the holes can be determined by the method set out herein below.

The sublayer (30) is compression resistant even after wetting, such that is its average caliper (34) loss (wet resilience) is less than 20% or even more preferably 12% or less, or even more preferably 10% or less, or even 8% or less, compared to the average caliper (34) of the dry sublayer (30) before wetting, under the same pressure. This is determined by the method set out herein below.

As described above, preferred diapers (10) herein have a sublayer (30) comprising at least two acquisition layers (a second layer (36) and first layer (37) and optionally further layers) with holes or indentations, whereby the holes (31) of the sublayer (30) are formed by holes in or through the (at least) two acquisition layers of the sublayer (30), as for example shown in FIGS. 2 and 12.

The acquisition layers (36, 37) of the sublayer (30) may also be such that the first layer (37) may comprise holes and the second layer (36) may have indentations that are formed into said holes, being thus also present on the z-direction and bottom side-walls of said holes of the first layer (37).

It may also be that the second layer (36) comprises through holes and the first layer (37) comprises blind holes, so that the holes (31) of the sublayer (30) are blind holes.

Alternatively, two or more of the layers (36, 37) of the sublayer (30) comprise through holes that form together the through holes (31) of the sublayer (30).

When the sublayer comprises a first and second acquisition layer (37, 36) and optionally further layers, it may be preferred that the surface areas of the x-y cross section of the holes through the second layer (36), or of the indentations in the second layer (36), are less than the corresponding surface areas of the x-y cross section of the holes in or through the first layer (37), measured on the surface of the first layer (37) that faces the second layer (36).

(Hereby, the x-y cross section of each hole in the second layer (36) is taken at the surface of the sublayer (30) that faces the wearer in use, and the x-y cross section of each hole in the first layer (37) is taken at the surface of that layer that faces the second layer (36), and so forth for subsequent layers).

In one embodiment (and in particular when the second acquisition layer (36) is not present on the z-direction extending walls of the holes of the first layer (37), as described below), it may be preferred that the surfaces areas of all x-y cross sections of a hole or indentation of the second layer (36) are smaller thane the surface areas of all x-y cross sections of a corresponding hole (or indentation) of the first layer (37), as shown in FIGS. 4, 5, 7 and 8.

Furthermore, the circumference of a hole or indentation in the second acquisition layer (36) is then preferably smaller than the circumference of the corresponding hole or indentation of the first acquisition layer (37).

For clarity, the x-y dimensions given for the combined holes (31) herein equal the x-y dimensions of the holes or indentations of the second acquisition layer (36), because they are taken on the surface of the sublayer (30) that faces the wearer in use.

Furthermore, it should be understood that the above does not have to apply to all holes (31), but it applies typically to at least 50% of the combined holes, preferably at least 90%, or even more preferably at least 95% or even 100% of the combined holes (31).

Highly preferred is that the (material of) the second acquisition layer (36) is not only present on the surface of the x-y direction extending wearer-facing surface of the first layer (37), but that it is also present on the substantially z-direction extending walls of the holes or indentations of the first acquisition layer (37), as shown in FIG. 9. This helps to reduce or avoid contact of unbonded or partially bonded fibers from the first acquisition layer (37) with the skin of the user.

It may also be optional that the (material of the) second acquisition layer (36) is also present on the bottom wall of the hole through or in the first acquisition layer (37); this may be achieved by providing indentations in the second layer (36), rather than holes.

When further acquisition layers are present, they may be present either underneath the first layer (37) (thus between the second layer and the backsheet) or underneath the second layer (36), and thus between the second layer (36) and first layer (37), or both. Such a further acquisition layer may have the same properties as the second or first layer. However, if a further acquisition layer comprises unbonded or partially bonded fibers, like the first layer (37), it would typically have holes with a circumference and x-y cross sectional surface areas that are smaller than the corresponding circumference or x-y cross sectional surface of the first layer, as described above.

The sublayer (30) may also comprise additional components, e.g. layers, which do not serve as acquisition layers, provided these components to not impede the formation or existence of the combined holes (31) described herein.

The first acquisition layer (37) has optionally a width and length that is smaller than the width and length of the further acquisition layers.

Preferred is the first acquisition layer (37) of the sublayer (30) comprises partially bonded or unbonded polypropylene (PP) and/or polyester fibres, preferably polyethylene terephthalate (PET) fibres. Alternatively, or in addition, it may be highly preferred that the first acquisition layer (37) comprises modified (cellulose) fibers, preferably chemically stiffened, twisted and/or curled (curly) (cellulose) fibers, preferably chemically stiffened, twisted and/or curled crosslinked cellulose or synthetic polymer fibres (preferably such cellulose fibres). Preferred may be materials available from Weyerhaeuser under as CMC520 and CMC517.

Also preferred may be that the first acquisition layer (37) comprises a multitude of bonded, carded bonded nonwoven layers, such as carded resin-bonded nonwovens, embossed carded resin-bonded nonwoven acquisition layers, and optionally highloft carded resin-bonded nonwoven acquisition layers, or preferably carded through-air-bonded nonwoven acquisition layers, carded thermo-bonded nonwoven acquisition layers; most preferably are non-embossed carded resin-bonded non-woven acquisition layers. Preferred are such materials with a high basis weight, i.e. of 40 gsm or more, preferably even 60 gsm or more.

Materials as above that may be used herein are available from BBA Fiberweb/Tenotex (Italy) under the trade name Printex AQL1 Phil (43 gsm, white); or from Freudenberg/Halifax under the code AL 1060 (SC V and SO, and AR10) and under the code114/011/05 (typically 43 or 60 gsm); or from Lohmann, under the trade name Paraprint.

The above-described carded nonwoven materials may also be suitably used as second acquisition layer for the sublayer (30) herein.

The sublayer (30) may be made by forming holes (31) in a continuous sublayer (30) (i.e. without holes (31)), for example by punching or pushing holes (31) in a said sublayer (30). If the sublayer (30) comprises two or more layers, then the holes (31) may be punched or pushed in two or more components or layers, either separately or at the same time.

For example, when the sublayer (30) comprises two or more acquisition layers (37, 36), it may be beneficial that the holes (31) are formed by pushing, e.g. by pushing a hole forming tool onto the surface of the second layer (36) and through the second and first layer (37) and further layers, such that part of the material of the second layer (36) is pushed into the holes, to cover (part of) the walls of the holes. This may provide smooth edges and walls of the holes (31), and furthermore it may inhibit the fibres of the first layer (37) to migrate into the holes (31). This embodiment whereby the second layer (36) is present on the walls of the holes (31) is shown in FIG. 9.

It may also be preferred to form the holes (31) of the sublayer (30) by laying down the material, e.g. fibres, of the sublayer (30) on a forming surface, around for example protrusions or around shaped portions that hereby shape the holes (31). For example, fibres may be laid down on a forming drum with protrusions in the required hole-pattern of the sublayer (30), around said protrusions to thus shape the holes (31), and the fibres may then optionally be bonded by known bonding techniques.

It may also be preferred that a first (37) and optional further layers with holes are first obtained and subsequently a second layer (36) is placed on top of the first layer and/and the second layer is partially pushed into the holes of the first (37) and further layers, to form the sublayer (30) described above.

It may also be preferred that the sublayer (30) comprises one or more layers formed by one of the methods above and one or more layers formed by a different method, as described above. For example, a sublayer (30) may comprise a first layer (37) formed by the lay-down technique above and a second layer (36) formed by punching or pushing, whereby the second holes (31) are punched or pushed either prior to combining the two or more layers, or after combining the two or more layers.

Topsheet (20)

The diaper (10) of the invention comprises preferably a topsheet, present on the sublayer, which in use is in contact with the skin of the user.

The topsheet may comprise a slit opening, to allow feces to pass to the sublayer (30).

In a preferred embodiment the diaper (10) comprises a topsheet (20) with apertures (21) to allow feces to migrate through the topsheet (20) to the sublayer (30).

It may be preferred that the holes (31) of the sublayer (30) have an average smallest dimension as defined herein that is larger than the average greatest dimension of the apertures (21) of the topsheet (20). The holes (31) of the sublayer (30) have typically a larger average surface area than the average surface area of the apertures (21) of the topsheet (20), as described above (although the total open area of the sublayer (30) may preferably be less than the total open area of the topsheet (20), as is shown in FIG. 12.

The sublayer (30) may have the same width and length dimensions as the topsheet (20), but it may be preferred that the sublayer (30) has a smaller width dimension and/or optionally a smaller length dimension than the topsheet (20). FIG. 1 shows such an execution whereby the width of the sublayer (30) is smaller than the width of the topsheet (20). FIG. 12 shows an embodiment whereby the length of the sublayer (30) is smaller than the length of the topsheet (20).

The topsheet (20) may be embossed, but in a preferred embodiment, the topsheet (20) is flat and the average caliper of the topsheet (20) equals the average caliper or depth of the apertures (21), as shown in FIG. 2.

The apertures (21) of the topsheet (20) are typically small, having an average greatest dimension (in the plane of the topsheet (20)) of from 2 to 8 mm, preferably from about 2 mm to 6 mm, or even more preferably from 2.4 to 6 mm, or even more preferably from 3 to 5 mm or to 4 mm.

Preferably, the apertures (21) have also an average smallest dimension of from 2 mm to 6 mm, and preferably from 3 to 5 mm.

The average aperture dimension when used herein is determined in the cross section of the apertures that is on the surface of the topsheet (20) that faces in use the body of the wearer, by the method said out below.

Preferably, the apertures (21) are such that the greatest dimension is through the centre point of the aperture (21). Preferably, the apertures (21) have an oval and/or circular circumference, as shown in FIGS. 1 and 2.

The average shortest (smallest) distance between the middle points of neighboring apertures (21) is preferably from 2 to 7 mm, or more preferred from 4 to 6 mm.

Each region (23) of apertures (21) has an open area, which is the sum of the surface areas of said apertures (21) of said region (23), as measured in the cross section of the apertures (21) in the body facing surface of the topsheet (20). This can be determined by the method described herein below.

This open area of each region (23) is preferably from 20% to 55% of the total surface area of said region, and preferably from 30% to 50%, or even more preferably from 30% to 45% thereof.

Preferably, at the total open area of the topsheet (20) (which is the sum of open area of the regions with apertures (21) of the topsheet (20)) is from 15% to 55%, and preferably from 20% to 50% or even more preferably from 25% or 30% to 45%, of the total surface area of the topsheet (20).

Preferably the topsheet (20) comprises a single region (23) with apertures (21) which is typically about 60% to 100% of the total surface area of the topsheet (20), preferably about 80% to 100% of the total surface area of the topsheet (20). Thus, in a preferred execution, the whole topsheet (20) comprises said apertures (21) and thus, there is only one region with apertures (21) in the topsheet (20) that is 100% of the topsheet (20) surface area, as is shown in FIGS. 1 and 2.

Another preferred execution, the topsheet (20) has one region (23) with apertures (21) that is centered in the topsheet (20), such that said region is not present along the longitudinal and transverse edges of the topsheet (20), i.e. so that no apertures (21) are present along said edges.

The topsheet (20) can be made of liquid permeable or impermeable material, because due to the apertures (21), the urine and feces will pass easily and quickly to the sublayer (30) and the absorbent core below. The topsheet (20) may be (made of) a nonwoven or woven web with apertures (21) that is made of synthetic and/or natural fibers, or it may be an apertured or apertured formed polymer film, or a combination thereof, as known in the art and for example described in U.S. Pat. No. 5,342,338 and EP-A-0203823.

Preferred apertured topsheets include fibrous nonwoven webs, made of polyolefin, preferably of polyethylene, polypropylene or copolymers thereof, or mixtures thereof.

Preferred topsheets (20) herein are made by forming apertures (21) in a continuous uninterrupted film or web of a thermoplastic polymer, for example polyolefins, and/or by providing a film or web with a plurality of spaced apart discrete bonds and weakening the web or film at a plurality of locations whereby a portion of the spaced part bonds are separated from said weakened locations, and subsequently applying a tensioning force to said web or film to rupture the weakened locations, e.g. by stretching said film or web, to form thus apertures.

Preferred processes for making apertured films or webs as used herein are described in U.S. Pat. Nos. 5,916,661, 5,658, 639 and 5,628,097.

The nonwoven webs with apertures (21) useful herein as topsheet (20) comprise preferably polyethylene and/or polypropylene and/or polyester fibers and preferably have a basis weight of about 15 to 30 g/m² or to 25 g/m².

The topsheet (20) is typically non-liquid retaining in use, to ensure the liquid (e.g. urine) is transported immediately through the topsheet (20) (the apertures (21) thereof and optionally through the topsheet (20) material itself) to the underlying acquisition sublayer (30) and absorbent core (11).

The topsheet (20) may comprise a skin care lotion as known in the art. It may be preferred that this is applied in the form of stripes on the topsheet (20), preferably in the form of longitudinal (Machine Direction) stripes.

The topsheet (20) may be completely or partially attached to the sublayer (30) described herein after. This may be done by any known method in the art, preferred methods include adhesive bonding. It may be preferred that the topsheet (20) and sublayer (30) are only partially attached to one another, for example 50% to 80% of the corresponding surface area between the topsheet and sublayer.

Unlike the sublayer (30) described above, the top sheet (20) is thin, e.g. less than 1.0 mm or typically even less than 0.5 mm thick, and may be hydrophilic or hydrophobic, because it merely serves to pass the liquid and feces directly through to the sublayer (30) below, and will typically not contain the liquid or distribute the liquid in x and y direction.

The topsheet (20) overlies the sublayer (30) either partially, or typically completely, as shown in FIGS. 1, 2 and 12. This includes the embodiment that the sublayer (30) has a smaller surface area than the topsheet (20), either having a smaller width (cross-machine direction) or length (machine direction) or both, as shown in FIGS. 1, 2 and 12.

Typically, at least one region (23) with apertures (21) of the topsheet (20) overlies a region with holes (31) of the sublayer (30), either partially or completely, such that an overlap-zone (40) exists, where at least some of the apertures (21) are positioned above at least some of the holes (31), completely and/or partially, to form combined apertures. (42).

The combined apertures (42) allow direct passage of feces (and liquids) from the user through the topsheet (20) into the holes (31) of the sublayer (30).

However, the region(s) (33) of the sublayer (30) and the holes (31) thereof, and the region (23) of the topsheet (20) and the apertures (21) thereof, and the overlap-zone (40) are created such that the amount of feces that can transfer back to the skin of the user is minimised, whilst still allowing the required passage of the feces to the holes (31) of the sublayer (30) and immobilisation and isolation of the feces in the holes (31) of the sublayer (30).

The overlap-zone (40) has thereto preferably an open area (which is the sum of the surface areas of the combined apertures (42) therein in the plane of the body facing surface of the topsheet (20)) of from 15% to 50% of the surface area of said overlap-zone, or preferably 20% to 45% or even more preferably 25% to 35%.

Typically, the total surface area of said overlap-zone (40) is at least 2 cm×3 cm (CD×MD) in order to have sufficient surface area to receive the feces and transport it through the apertures (21) into the holes (31). Hereby the width and length dimensions of 2×3 cm are average values. (More than one overlap zone (40) may be present and than the total of the overlap zones (40) should be at least 2 cm×3 cm as above, but preferably each overlap zone (40) is at least 2 cm×3 cm as above.)

Preferred is that the overlap zone (40) is present in the back and crotch portions of the diaper, or part thereof, but not in the front portion of the diaper.

In a preferred embodiment, the absorbent diaper (10) has one single overlap zone (40), and preferably also only one region (33) of holes (31) in the sublayer (30), and the topsheet (20) overlays this region completely, and then this single overlap zone (40) is preferably at least positioned in the crotch (43) and/or back portion (44) of the diaper, as described above, as shown in FIG. 12, e.g. in the back 70% of the surface area of the diaper (10) or topsheet (20) thereof.

The overlap zone (40) may have any shape, including circular, oval, rectangular, triangular, or square. Since the region (33) of the sublayer (30) is typically smaller in surface area than the region (23) of the topsheet (20), the shape of the overlap area is typically determined by the shape of the sublayer (30), as shown in FIGS. 8, 9 and 10.

The sublayer (30) (and/or the topsheet (20)) may comprise registrable marks that allow registration of the sublayer (30) and its holes (31) thereof (and/or the topsheet (20) and its apertures (21)) to allow correct alignment and/or partial alignment of the holes (31) of the sublayer (30) and the apertures (21) of the topsheet (20).

Test Methods Referred Herein

Caliper (34, 35)

The caliper of (the topsheet (20) and) the sublayer (30), or the part thereof that is present in the overlap zone, and of the apertures (21) or holes (31) thereof are determined by use of a (calibrated) Micrometer, under 23° C. and 50% humidity conditions, whereby the Mircometer as an accuracy minimum of 0.01 mm, lowering speed of 3 mm/s, dwelling time of 2-5 sec., such as for example a Frank Type 16303 available from Twing Albert-Frank Gmbh. The Micrometer has a loading 266 grams and an anvil 40 mm in diameter (resulting in 0.3 psi).

The material to be measured is equilibrated for at least 2 hours at 23° C. and 50% humidity prior to the measurement. If the material is to be cut prior to the measurement, the cutting should be done such that the caliper does not change, e.g. without compression in the area that is to be measured. The material should be free of wrinkles, folds, or defects in the area that is to be measured.

The material is placed under the micrometer and the caliper is recorded after the dwelling time.

Five samples can be made and measured to calculate the average over five samples, which is referred to herein.

Caliper (34) Loss After Wetting (Wet Resilience)

The following test method determines the wet resilience of the sublayer (30) under a pressure of 0.3 psi, after wetting the sublayer (30), and this is translated in the caliper loss values referred herein.

The sublayer (30) and topsheet (20) are removed from the absorbent diaper (10). (For measurement purposes, the topsheet (20) is included in this measurement, but the caliper values of the topsheet (20) are deducted, as described below).

In some embodiments, the sublayer (30) may be enclosed between an absorbent core cover (13) and the topsheet (20), in particular when the sublayer (30) is not a web or film, but comprises for example only partially bonded or non-bonded fibers. If such a core cover or core wrap (13) is present, this should be removed from the diaper together with the sublayer (30) and the topsheet (20), to obtain the sample used herein, containing the core cover (13), sublayer (30) and topsheet (20).

The samples are conditioned for 2 hours at 23° C., 50% humidity and the tests are conducted at the same conditions.

Then, the weight of each sample is determined by any standard method.

First, under a pressure of 0.3 psi, the caliper (34) of the dry sample as a whole and the caliper of the topsheet (20) and optionally the core cover are determined. The caliper (34) under said pressure of the topsheet (20) and optionally the core wrap (13) are deducted from the overall caliper, to obtain the caliper (34) under pressure of the dry sublayer (30). The caliper of the sublayer (30) and topsheet (20), and optionally the core cover (13), are measured in the overlap zone (40), by measuring the caliper thereof in at least 3 points and taking the average thereof (hereinafter referred to as the (average) dry caliper (34) under pressure). The same is done for the caliper under pressure of the topsheet (20) and optionally the core cover (13) (which may be combined into one set of measurements to obtain their combined average caliper under pressure).

Then the dry calipers are measured as set out above, with a Micrometer (e.g. Frank type 16303) with a pressure foot diameter of 40 mm, with a pressure of 0.3 psi, with a lowering speed of 3 mm/s.

Caliper readings are taken 1 minute after the pressure foot is contacted with the surface of the sample.

Then, the sample is loaded with 10 ml saline solution (0.9% NaCl in de-mineralized water) per gram sample, by gently pouring the saline solution along the y-direction centre line of the sample, by slowly moving up and own along said centre line and pouring the saline with a speed of approximately 1 ml/sec. Then the caliper of the sample and the topsheet (20) and optionally core wrap at exactly the same points as before, but after wetting is determined as described above.

The average dry and wet calipers of the sublayer, as referred to herein are calculated as follows:

Average Dry Caliper of the Sublayer=(average dry caliper of the sample comprising sublayer, topsheet, and optionally the core wrap)−(average dry caliper of the topsheet plus optionally core wrap).

Average Wet Caliper of the Sublayer=(average wet caliper of the sample comprising sublayer, topsheet, and optionally the core wrap)−(average wet caliper of the topsheet plus optionally core wrap).

The percentage caliper (34) loss is then calculated as follows:

$$\frac{(\text{Av. Dry Caliper of the Sublayer}) - (\text{Av. Wet Caliper of the Sublayer})}{(\text{Av. dry caliper of the Sublayer})} \times 100\%$$

Open Area Determination; Aperture and Hole Dimensions and Surface Areas Determination The open area of the regions (23, 33) of the sublayer (30), topsheet (20) and of the overlap-zone (40) as used herein can be determined by light microscopy as follows.

Depending on the size of the region (23, 33) or overlap zone (40), said region or overlap zone (40) is each analyzed either as a whole, or in separate portions, to reach an open area value of the whole region (23, 33) or overlap zone (40).

To determine the open area of the overlap zone (40), a sample is prepared by taking the topsheet (20) and the sublayer (30) to be analyzed from the absorbent diaper, in such a manner that they do not move with respect to one another, in order to keep the overlap-zone (40) the same. Alternatively, the sublayer (30) and topsheet (20) are first marked such that after removal from the diaper, the topsheet (20) can be placed onto the sublayer (30) in its original position, to obtain the same overlap zone (40).

Then, the open area and aperture dimensions of the overlap zone (40) can be determined (by measuring and viewing the surface area that in use faces the user).

To determine the open area and aperture/hole dimensions of the topsheet (20) and sublayer (30), these will have to be separated in the above sample, or new samples of the topsheet (20) and sublayer (30) will have to be made for analyses.

Any sample size can be submitted to the light microscopy, but typically the sample will not be bigger than 15×15 cm. If the region and/or sublayer (30) is or are bigger than this, they may be cut into separate samples by any suitable technique, and each sample can be measured.

The light microscope (JAI CV-M1 E Monochromic Camera; with as lens a Micro-zoom-0.1-0.7) is connected to an interface (ITI-Vision-Itex) that is connected to a computer that runs Optimas software (Media Cybernetics, L.P. Optimas version 6.51) that will do all calculations. Any suitable external light source may be used, for example Kaiser e-Vision.

The sample is placed onto a black cardboard without stretching, without wrinkles or folds. This is placed under the light microscope and the zoom is adjusted to 3.5 and focused until a clear picture is obtained. Then the sample is removed and a ruler is placed under the microscope.

The calibration is then started with the software.

The software will calculate the average smallest and greatest aperture or hole sizes in the cross sections of the apertures and holes on the surface, and the total or average open areas thereof.

The measurement can be repeated twice to obtain 3 values and an average thereof, which is referred herein throughout the specification.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A diaper or adult incontinence garment for the acquisition and storage of bodily exudates, the diaper or adult incontinence garment comprising:
   a. a topsheet, a backsheet, and an absorbent core disposed between the topsheet and the backsheet; and
   b. a sublayer configured to store and/or immobilize feces disposed between the topsheet and the absorbent core, the sublayer comprising first and second fibrous acquisition layers arranged in a face to face relationship, a wearer facing surface, and an opposing garment facing surface, each of the first and second fibrous acquisition layers including one or more regions having a multitude of holes, at least some of the holes being blind holes and at least some of the holes being through holes, wherein at least some of said through holes in said first acquisition layer and some of said through holes in said second acquisition layer form combined holes, wherein the circumference of the through holes in the second acquisition layer is smaller than the circumference of the corresponding through holes in the first acquisition layer, said region(s) having a total open area of from 10% to 50% of the total surface area of said sublayer, as measured on the user facing surface, said sublayer having a length in the y-direction, width in the x-direction and caliper in the z-direction, said holes having an average smallest diameter in an x-y cross section of the holes in the wearer facing surface of said sublayer of at least 3 mm, said sublayer having an average caliper of from 2 mm to 8 mm, and said sublayer having an average caliper loss after wetting and under pressure of 0.3 psi of less than 20%.

2. The diaper or adult incontinence garment of claim 1, wherein said average caliper loss is 12% or less.

3. The diaper or adult incontinence garment of claim 1, wherein said holes have an average minimum diameter of from 4 mm to 7 mm, and said sublayer has an average caliper of between 3.5 and 5 mm.

4. The diaper or adult incontinence garment of claim 1, wherein said acquisition layer comprises a material selected from the group consisting of chemically modified stiffened curled fibrous material, partially bonded polyester fibers, non-bonded polyester fibers, cellulose pulp, a multitude of carded bonded nonwoven layers having a basis weight of at least 40 gsm each, and mixtures thereof.

5. The diaper or adult incontinence garment of claim 1, wherein said sublayer comprises at least one of chemically modified and stiffened curled fibrous cellulose material.

6. The diaper or adult incontinence garment of claim 1, further comprising at least one of a topsheet with apertures and a topsheet with a slit opening.

* * * * *